United States Patent
Mantovani

(10) Patent No.: US 10,231,726 B2
(45) Date of Patent: Mar. 19, 2019

(54) PERFECTED DEVICE FOR THE TRANSOSSEOUS INSERTION OF SUTURE THREADS

(71) Applicant: NCS LAB S.R.L., Carpi (Modena) (IT)

(72) Inventor: Matteo Mantovani, Reggio Emilia (IT)

(73) Assignee: NCS LAB S.R.L., Carpi (IT)

( * ) Notice: Subject to any disclaimer, the term of this patent is extended or adjusted under 35 U.S.C. 154(b) by 60 days.

(21) Appl. No.: 14/900,368

(22) PCT Filed: Jun. 18, 2014

(86) PCT No.: PCT/IB2014/062338
§ 371 (c)(1),
(2) Date: Dec. 21, 2015

(87) PCT Pub. No.: WO2015/008176
PCT Pub. Date: Jan. 22, 2015

(65) Prior Publication Data
US 2016/0143635 A1 May 26, 2016

(30) Foreign Application Priority Data
Jul. 17, 2013 (IT) .............................. MO2013A0206

(51) Int. Cl.
*A61B 17/04* (2006.01)
*A61B 17/17* (2006.01)
*A61B 17/00* (2006.01)
*A61B 17/06* (2006.01)
*A61B 17/29* (2006.01)

(52) U.S. Cl.
CPC .......... *A61B 17/0469* (2013.01); *A61B 17/04* (2013.01); *A61B 17/0482* (2013.01);
(Continued)

(58) Field of Classification Search
CPC ............ A61B 17/0469; A61B 17/0482; A61B 17/0483; A61B 17/04; A61B 17/1714;
(Continued)

(56) References Cited

U.S. PATENT DOCUMENTS

| 9,763,659 B2 * | 9/2017 | Sholev ............... A61B 17/0482 |
| 2010/0106056 A1 * | 4/2010 | Norris ................. A61B 8/0841 600/567 |

(Continued)

FOREIGN PATENT DOCUMENTS

| EP | 2 554 129 A1 | 2/2013 |
| WO | 2010/056785 A2 | 5/2010 |

(Continued)

*Primary Examiner* — Todd J Scherbel
*Assistant Examiner* — Brooke Labranche
(74) *Attorney, Agent, or Firm* — Pearne & Gordon LLP

(57) ABSTRACT

The invention concerns a perfected device for the transosseous insertion of suture threads. This device comprises a main body (1) supporting a protruding cannula (3) provided with an active end (30); the device comprises a flexible threadlike element (4), on which there are fashioned a sharp tip (40) and an opening (41) that serves for the threading of at least one suture thread (5), said element (4) being housed in a coaxially sliding manner inside said cannula (3) and, on command, exiting from the active end (30) of the cannula, assuming a curved position; the device comprises first means for producing the coaxial movement of the threadlike element (4) in the two directions with respect to the cannula (3) and second means for producing a coaxial movement of the threadlike element in the exiting direction from the cannula (3); for a short tract, the movement produced by the second means is disengaged from the advancement of the threadlike element produced by the first means.

5 Claims, 4 Drawing Sheets

(52) U.S. Cl.
CPC ...... *A61B 17/0483* (2013.01); *A61B 17/1714* (2013.01); *A61B 17/1764* (2013.01); *A61B 2017/00367* (2013.01); *A61B 2017/0608* (2013.01); *A61B 2017/06042* (2013.01); *A61B 2017/06095* (2013.01); *A61B 2017/2915* (2013.01); *A61B 2017/2924* (2013.01)

(58) Field of Classification Search
CPC ........... A61B 2017/00367; A61B 2017/06042; A61B 2017/0608
See application file for complete search history.

(56) References Cited

U.S. PATENT DOCUMENTS

| | | |
|---|---|---|
| 2010/0121337 A1 | 5/2010 | Pandya |
| 2010/0121338 A1 | 5/2010 | Pandya |
| 2010/0121354 A1 | 5/2010 | Pandya |
| 2010/0121375 A1 | 5/2010 | Pandya |
| 2011/0118746 A1 | 5/2011 | Fischer et al. |
| 2011/0118760 A1* | 5/2011 | Gregoire ............ A61B 17/0483 606/145 |
| 2012/0109156 A1 | 5/2012 | Overes et al. |
| 2013/0046338 A1 | 2/2013 | Suzuki et al. |
| 2013/0178854 A1* | 7/2013 | Sholev ............... A61B 17/0469 606/79 |
| 2014/0135802 A1 | 5/2014 | Mantovani |
| 2014/0303625 A1 | 10/2014 | Sholev et al. |

FOREIGN PATENT DOCUMENTS

| | | |
|---|---|---|
| WO | 2012/007941 A2 | 1/2012 |
| WO | 2013/014553 A1 | 1/2013 |
| WO | 2013027209 A1 | 2/2013 |

\* cited by examiner

PERFECTED DEVICE FOR THE TRANSOSSEOUS INSERTION OF SUTURE THREADS

The object of the present invention is a perfected device for the transosseous insertion of suture threads.

Specifically, but not exclusively, the device represents a tool conceived to help a surgeon in positioning suture threads through bones. In particular, it reveals its usefulness in many operations requiring transosseous suture threads to be disposed along non-rectilinear "paths". Typical examples of these types of operations are those performed to repair lesions of rotator cuff tendons.

A known device of this sort is described in patent application no. WO 2013/014553 filed by the same Applicant and which, briefly stated, comprises a body that supports a protruding cannula in which a flexible threadlike needle with shape memory is housed in a sliding manner, the end of which reacquires a curved form when the needle exits the cannula; on command by a screw device, the needle is pushed, exiting the cannula so as to penetrate a zone of the tissue to be sutured and emerge in another zone of the tissue to be sutured, creating a curved hole between the two zones to be sutured and through which the suture thread passes.

One drawback of the known device is represented by the fact that in the fairly frequent case in which needle insertion must be facilitated by light manual tapping on the rear end of the device, this light tapping affects the entire structure of the device and causes undesirable and harmful pressure on the end of the cannula from which the needle exits onto the bone tissue to be perforated.

Another drawback of the known device is represented by the fact that in spite of the presence of an indicator device, the position of the needle exit point is not always the position foreseen owing to possible angular movements that the operator can inadvertently impart to the device and thus to the needle, during the procedure for penetration of the tissue to be sutured.

The aim of the present invention is to overcome the drawbacks of the prior art by offering a device that does not produce undesirable pressure of the end of the cannula on the bone tissue to be perforated and that enables precise predetermination of the exit point of the needle from the tissue to be sutured.

This and other aims and advantages are all achieved by the invention at hand as characterized in the claims.

Further characteristics and advantages of the present invention will be made more apparent in the detailed description herein below of an embodiment of the invention at hand, which is illustrated by way of non-limiting example in the accompanying figures, in which.

Figure 1:
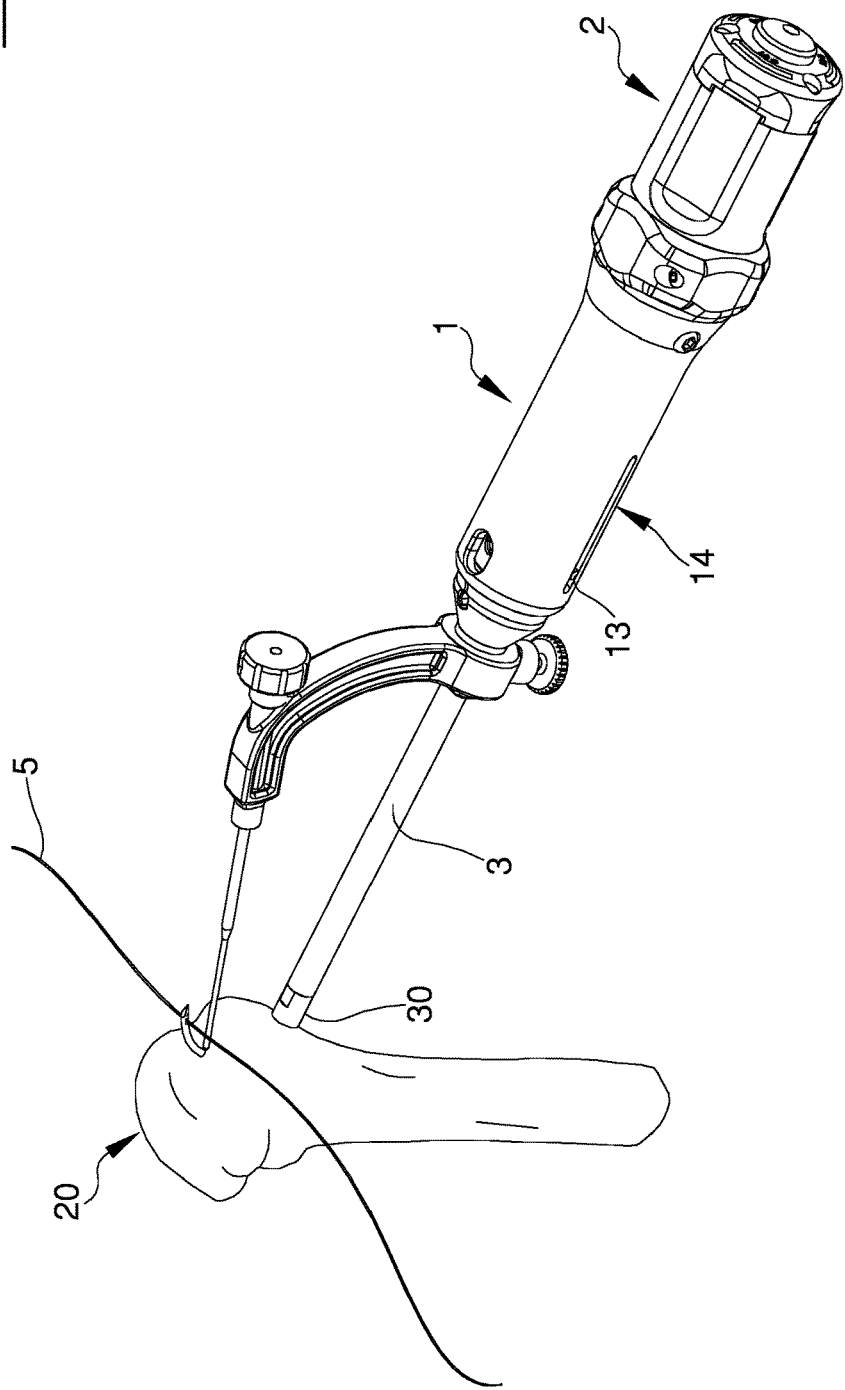
FIG. 1 is a schematic, perspective overall view of the device at hand.
Figure 2:
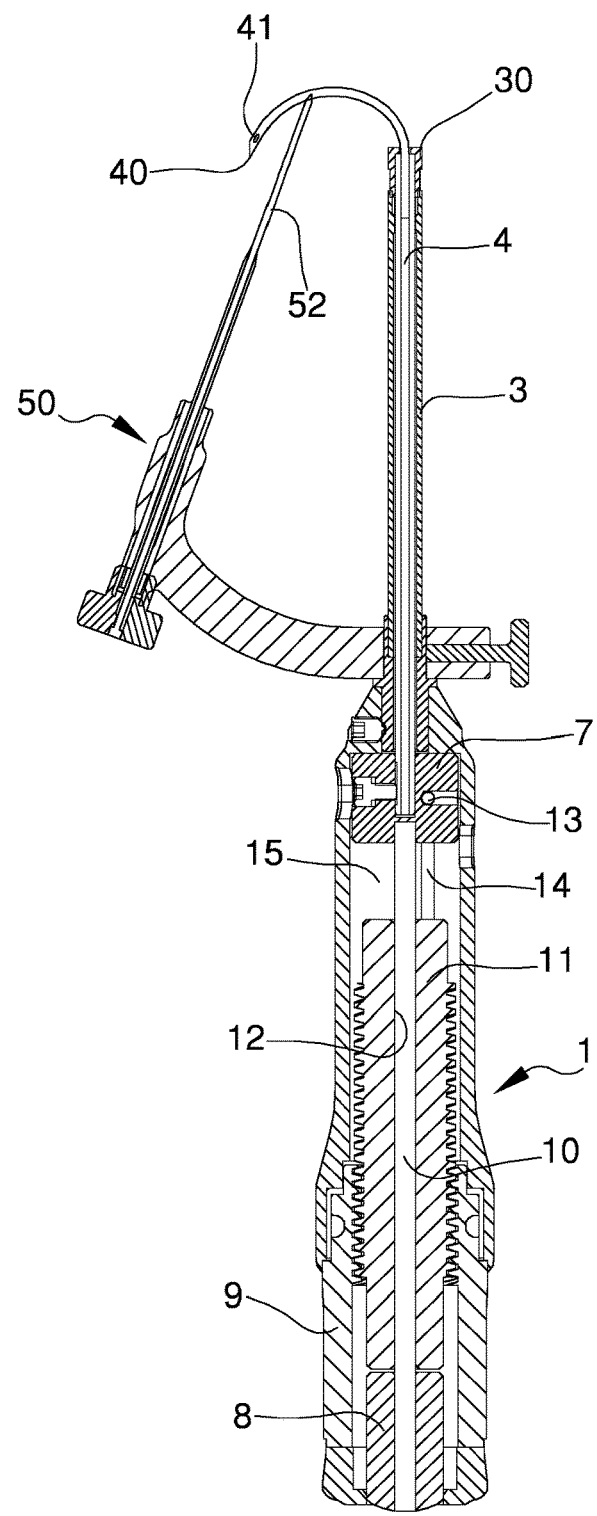
FIG. 2 is a schematic longitudinal section of the device with the threadlike element outside the cannula.

With reference to the accompanying figures, the main body of a device for transosseous insertion of suture threads 5 is indicated by the number 1.

The main body 1 is equipped with a grip 2 and bears, integrally supported, a cannula 3, which is protruding and provided with an active end 30 specifically configured to enable it to be rested on the bone surface.

A flexible threadlike element 4 is housed in a coaxially sliding manner inside the cannula 3 and it is suitable for exiting, on command, from the active end 30 of the cannula 3.

The threadlike element 4 has the property of freely assuming, that is, when not sheathed in the cannula 3 and at least in an adequate temperature range for which its operative use is foreseen—this temperature range comprising room temperature—a natural and predetermined curved form at least in a given portion of the terminal part thereof.

The threadlike element 4 has particular properties and is made of a super-elastic, shape-memory material, for example an alloy of nickel and titanium; the characteristics of the alloy impart superelasticity and shape memory so that the pre-established curved form appears at least in the terminal part of the threadlike element 4 once the latter is no longer contained inside the cannula 3.

The threadlike element 4 is provided, at the free end thereof, with a sharp tip 40, which realizes and facilitates the perforation of bone tissue. The tip 40 is schematically represented in FIG. 1 by a structure 20, and at the free end of the sharp tip, a small eye-like opening or eyelet 41 suitable for threading at least one suture thread 5 is afforded.

The above description referring to the device at hand is shared in common with the known device disclosed in patent no. WO 2013/014553.

The device at hand comprises a first means for producing the coaxial movement of the threadlike element 4 in the two directions with respect to the cannula 3 and a second means for producing a coaxial movement of the threadlike element in the direction for exiting the cannula 3; the advancement movement for the exiting of the threadlike element produced by the second means is disengaged for a short tract from the advancement movement produced by the first means.

Said second means comprises a first element 7, to which, by means of a grub screw, the threadlike element 4 is coaxially fastened at the end thereof facing the interior of the main body; the first element 7 is slidably coupled inside the main body 1 in the proximity of the front part of the main body.

Said second means further comprises a second element 8 that is slidably coupled with the main body 1 and that exits at least partially from the rear part 9 of the main body, that is, from the grip 2.

A connecting rod 10 of a smaller cross-section than the cross-section of the first and second elements is arranged inside the main body 1. The rod 10 is coaxially fastened to the first element 7 and to the second element 8 and thus solidly constrains these two elements in axial translational motion inside the main body 1. An annular cavity 15 is thus defined in the internal central zone of the main element; the cavity 15 is defined at either end by the first element 7 and by the second element 8 and the rod 10 passes through it.

A pawl 13 is fastened to the first element 7 and it can slide in a through slot 14 longitudinally fashioned on the main body 1, following axial movement of the first element 7; this prevents the first element from rotating about its own axis during use of the device.

The second means described above is paired with the first means, which, as mentioned previously, serves to produce the coaxial movement of the threadlike element 4 in the two directions with respect to the cannula 3.

This first means comprises a rear part 9 of the main body that is free to rotate with respect to the remaining part of the main body and it is coupled, with a threaded coupling, to a slider 11 comprising a through hole 12 in which the rod 10 is inserted in a freely slidable manner. The slider 11 can slide in an axial direction inside the main body 1 and particularly inside the annular cavity 15.

The axial length of the slider 11 is shorter than the axial distance existing between the first element 7 and the second element 8.

In summary, the slider and the set of elements made up of the first and second element joined by the rod 10 are constrained to each other so as to slide with respect to each other; the maximum stroke of their relative sliding movement is defined by the axial distance between the first 7 and second element 8 and the axial length of the slider 11.

As stated previously, the device at hand serves for the transosseous insertion of suture threads; for this purpose, the end of the threadlike element must be inserted in the bone tissue at a pre-established point and the bone tissue perforated so as to pass the threadlike element inside the tissue and have the end thereof exit at another point on the bone tissue, this point also being pre-established. As is also the case with known devices, along its path within the bone tissue, freeing itself from the containment of the cannula 3, the threadlike element 4 reacquires the curved configuration, by virtue of shape memory, enabling the sharp tip 40 to realize, during penetration, a curved path that passes through the bone until the sharp tip exits therefrom.

Figure 3:
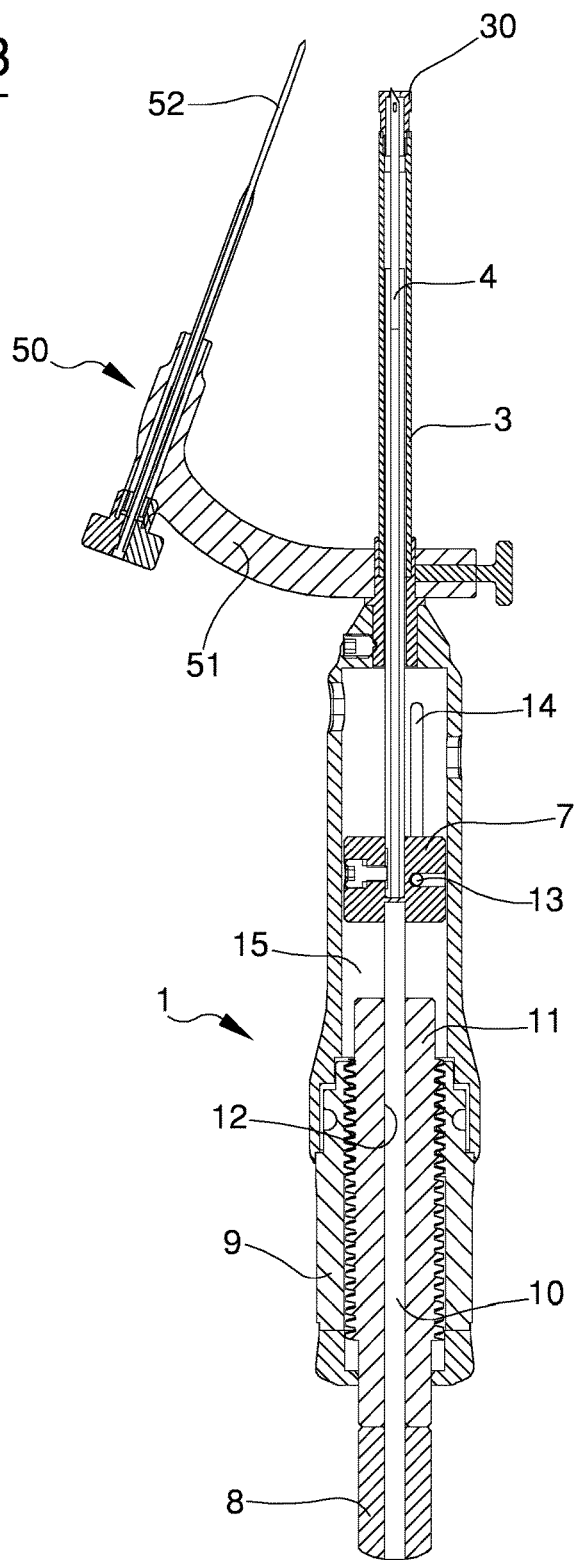
FIG. 3 is a schematic longitudinal section of the device with the threadlike element inside the cannula.
Figure 4:
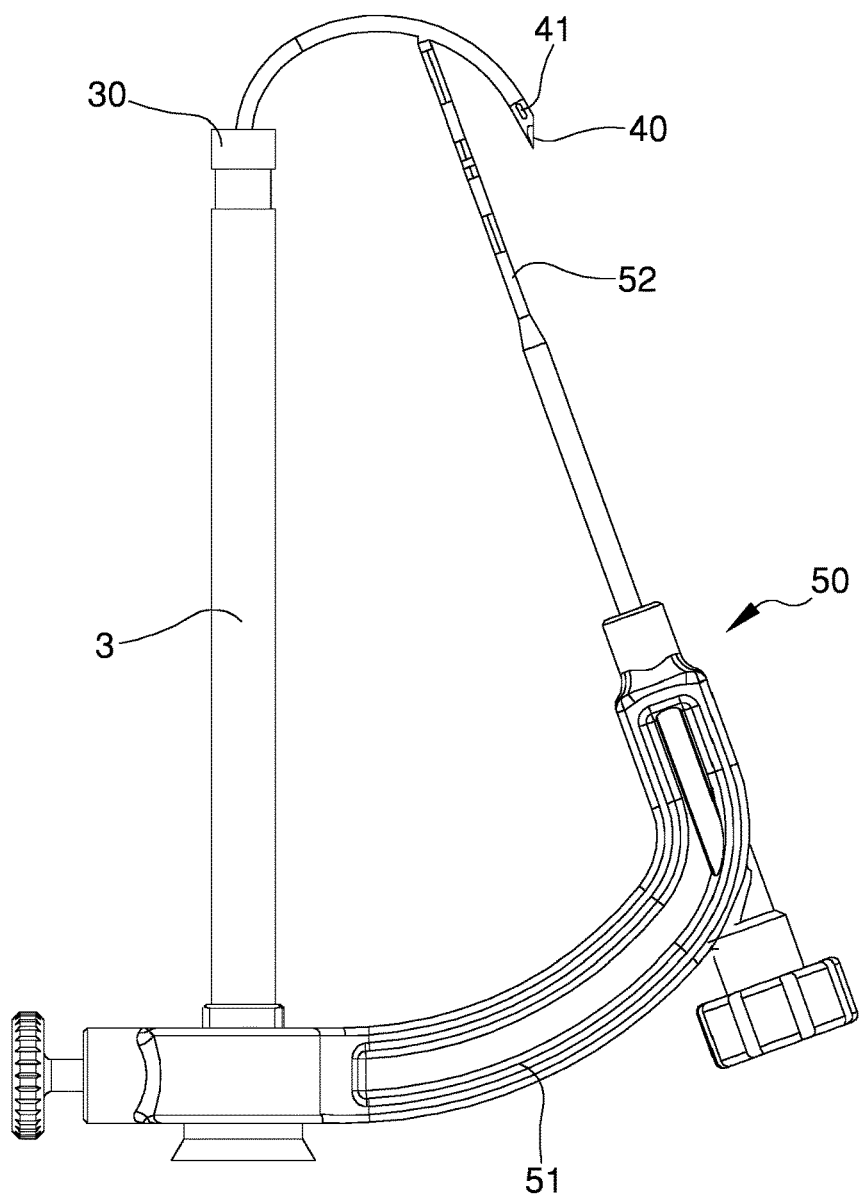
FIG. 4 shows the collimator of the device at hand, with some parts sectioned.

To perform the described procedure, one begins from an initial configuration, which is illustrated in FIG. 3, in which the threadlike element 4 is completely contained inside the cannula 3, the first element 7 of the second means is inside the chamber in the proximity of (or in contact with) the slider 11, and the second element 8 of said means protrudes from the rear part of the device. The active part 30, with the sharp tip 40 of the threadlike element inside it, is rested on the bone surface to be perforated. With a light tap on the element 8, the tip 40 is then inserted in the bone tissue. This procedure, which is carried out with the second movement means does not entail any stress on the bone tissue by the active end 30 rested against the bone tissue, given that the tap on the element 8 only causes the element 8 and the elements connected to it, that is to say, the rod 10, the first element 7 and the threadlike element 4 to slide. No pressure at all is exerted on the remaining part of the device or on the active part 30 thereof in particular.

One then acts upon the first movement means by rotating the rear part 9 so as to advance the slider 11. When the front part of the slider comes into contact with the element 7, the element 7 is pushed forward, together with all the elements connected to it and it causes the threadlike element 4 to advance into the bone tissue. In this step, upon freeing itself from the containment of the cannula 3, the threadlike element 4 reacquires the curved configuration, by virtue of shape memory, enabling the sharp tip 40 to realize, during penetration, a curved path that passes through the bone until the sharp tip exits therefrom.

If during penetration through the bone tissue, problems with advancing the threadlike element in the bone tissue are encountered and stronger pressure is needed in the direction of advancement, light taps can be exerted on the element 8 again to facilitate insertion of the tip 40 into the bone tissue. In this case as well, this procedure does not entail any stress on the bone tissue by the active end 30 rested against the bone tissue, given that the tapping on the element 8 only causes the second element 8 and the elements connected to it to slide. Following these tapping procedures on the element 8, the first element 7 detaches from the end of the slider 11, sliding forward; subsequent reactivation of the first movement means restores contact between the end of the slider and the first element 7, and thus normal advancement of the threadlike element 4.

A collimator 50 is provided to define the exact exit point of the sharp tip 40 from the bone tissue and it is firmly connected to the active end 30 of the device by means of a support 51. A through hole enabling insertion of a needle 52 is fashioned on the support 51 and the needle is arranged coplanar with the cannula 3, particularly coplanar with the plane containing the curved end of the threadlike element, and it is inclined with respect to the curved end. When the end of the threadlike element is outside the cannula and assumes its curved configuration, the tip of the needle 52 is rested against a point of the curve of the end of the threadlike element so as to define the exact position of this point and keep this point fixed even when the threadlike element is inside the cannula.

When beginning the suturing procedure, the tip of the needle 52 is positioned on the bone tissue at the point from which one intends to have the tip 40 of the threadlike element exit; the threadlike element is inside the cannula. The active end 30 of the device is then rested against the bone tissue at a point selected by the operator on a spherical surface having the point of contact of the tip of needle 52 with the bone tissue as the centre. Whatever point is selected by the operator (obviously among the points indicated above), it is certain that the exit point of the tip 40 of the threadlike element will be the desired point. Furthermore, if the operator tends to cause accidental undesirable movement of the device, for example a slight rotation about the axis of the device, keeping the tip of the needle 52 fixed will prevent such movement. In any case, if this undesirable movement were to take place, the shifting of the tip of the needle 52 from the predetermined point would immediately alert the operator who could instantly correct the position of the device and return it to the desired position.

The invention claimed is:

1. A perfected device for the transosseous insertion of suture threads, comprising: a main body (1) equipped with a grip (2), and supporting a protruding cannula (3) provided with an active end (30); a flexible threadlike element (4), whereon there are fashioned a sharp tip (40) and an opening (41) that serves for the threading of at least one suture thread (5), said element (4) being made of a shape-memory alloy material and being housed in a coaxially sliding manner inside the cannula (3) and, on command, exiting from the active end (30) of the cannula (3); wherein the end protruding from the cannula of the threadlike element freely assumes a natural and predetermined curved form; a first means for threadingly producing the coaxial movement of the threadlike element (4) in two directions with respect to the cannula (3); a second means for producing a coaxial movement of the threadlike element, in the exiting direction from the cannula (3) and that for a short tract is disengaged from the advancement of the threadlike element produced by the first means; wherein the first means comprises a rear part (9) of the main body (1) and a slider (11); wherein said second means comprises: a first element (7), whereto the threadlike element (4) is fastened, said element (7) being slidably coupled inside the main body (1) in the proximity of the front part thereof; a second element (8) slidably coupled to the main body (1) and that exits at least partially from the rear part (9) of the main body (1); a connecting rod (10), of a smaller cross-section than the cross-section of said first element (7) and said second element (8) and that is arranged inside the main body (1) and solidly constrains the first element (7) and the second element (8) in translational motion; wherein the rear part (9) of the main body is free to rotate (a) around an axis parallel to a longitudinal axis of the cannula (3) and (b) with respect to the remaining part of the main body and it is coupled, with a threaded coupling, to the slider (11) that can slide in an axial direction inside the main body (1) and wherein said rear part (9) which is free to rotate comprises a through hole (12) in which the connecting rod (10) is inserted in a freely slidable manner; the axial length of the slider (11) is shorter than the axial distance existing between the first element (7) and the second element (8).

2. The device according to claim 1, characterized in that the device comprises a pawl (13) that is fastened to the first element (7) and can slide in a through slot (14) longitudinally fashioned on the main body (11).

3. The device according to claim 1, characterized in that the device comprises a collimator (50) firmly connected to the active end (30) of the device by means of a support (51); a through hole for insertion of a needle (52) is fashioned on the support (51), the needle is arranged coplanar with the cannula (3) and the tip of the needle is rested against a point of the curve of the end of the threadlike element in its position external to the cannula (3) so as to define and keep the exact position of this point fixed.

4. The device according to claim 1, wherein the shape-memory alloy material is a super-elastic material.

5. The device according to claim 1, wherein the threadlike element (4) is made of an alloy of nickel and titanium.

\* \* \* \* \*